United States Patent [19]

Unangst

[11] Patent Number: 5,089,271
[45] Date of Patent: Feb. 18, 1992

[54] STABILIZED ANTIBIOTIC COMPOSITIONS FOR ANIMAL FEEDING

[75] Inventor: R. Richard Unangst, Havertown, Pa.

[73] Assignee: SmithKline Beecham Corporation, King Prussia, Pa.

[21] Appl. No.: 408,825

[22] Filed: Sep. 18, 1989

[30] Foreign Application Priority Data

[74] 825091899

[51] Int. Cl.$^5$ ............................................... A61K 9/16
[52] U.S. Cl. ...................................... 424/490; 424/442; 424/494; 424/495; 424/497; 424/498
[58] Field of Search ............... 424/442, 498, 494, 495, 424/497

[56] References Cited

U.S. PATENT DOCUMENTS

| | | | |
|---|---|---|---|
| 2,890,980 | 6/1959 | Hotchkiss et al. | 424/442 |
| 3,531,563 | 9/1970 | Klothen et al. | 424/442 |
| 3,627,885 | 12/1971 | Rondelet et al. | 424/177 |
| 3,697,640 | 10/1972 | Grant et al. | 424/494 |
| 3,829,564 | 8/1974 | Merry et al. | 424/442 |
| 4,513,019 | 4/1985 | Brancq et al. | 424/494 |
| 4,606,940 | 8/1986 | Frank et al. | 424/494 |
| 4,808,412 | 2/1989 | Smith et al. | 424/442 |

*Primary Examiner*—Thurman K. Page
*Assistant Examiner*—William E. Benston, Jr.
*Attorney, Agent, or Firm*—William T. King; Edward T. Lentz

[57] ABSTRACT

Stabilized antibiotic composition for animal feeds which provide for improved recovery of the antibiotic from the animal feed. The compositions contain the antibiotic in a coated form. In a preferred embodiment the antibiotic is coated by microencapsulation before being added to the animal feed.

4 Claims, No Drawings

STABILIZED ANTIBIOTIC COMPOSITIONS FOR ANIMAL FEEDING

This invention relates to antibiotic animal feeds which provide for an improved recovery of the antibiotic from the feed upon analysis. More particularly, the invention is concerned with a method of improving the recovery of virginiamycin from animal feeds which contain ingredients which bind or interferes with the analysis of virginiamycin.

BACKGROUND

The problem involved in the low recovery of antibiotics from animal feeds is a complex one and has long been recognized as a major problem facing the manufacturers and users of animal feeds. For example, the manufacturer may face problems with regulatory authorities because the initial assays are out of specifications or allowable limits. In some countries this may result in fines for the manufacturer. A low antibiotic initial assay also leads to customer dissatisfaction.

The low recovery of antibiotics such as virginiamycin from animal feeds is enhanced by the fact that modern day feeds, which are more aggressive, contain significantly higher levels of moisture, fat, ethoxyquin, meat and bone meal, fish meal, coccidiostats and trace minerals than do the normal feeds.

By aggressive feeds is meant those feeds which contain higher levels of ingredients which have a detrimental or completing effect on antibiotics than do normal feeds. For example, normal poultry feeds contain up to 4 percent fat. Aggressive poultry feeds contain above 5 percent fat. Normal cattle feeds contain about 8 to 10% moisture whereas aggressive cattle feeds contain 15-30% moisture.

High moisture grains have become economically competitive. Further, modern day feeds provide for a cheaper form of proteins by the addition of meat and bone meal and fish meal. The addition of a higher percentage of fat to poultry feeds results in high energy levels. These levels are required by today's poultry due to their faster growth rate.

Many attempts have been made to increase the virginiamycin recovery from the above noted aggressive animal feeds. One such attempt was granulating the antibiotic before adding it to the basic animal feed. This method is set forth in U.S. Pat. No. 3,627,885. The animal feed having granulated virginiamycin present is known as Stafac. The granulated virginiamycin did improve recovery from normal feed compositions over plain virginiamycin. However analysis of the aggressive feeds containing granulated virginiamycin resulted in low recovery and fell outside of allowable limits.

It is therefore an object of this invention to provide aggressive animal feeds containing antibiotics which upon analysis result in a high recovery of the antibiotic.

It is a further object of this invention to improve the recovery of virginiamycin from animal feeds which contain high levels fat, moisture, and other deleterious ingredients noted above which effect the recovery of the virginiamycin.

In accordance with this invention it has been discovered that when virginiamycin is coated before being added to the basic aggressive feed, a very significant improvement in recovery of the compound upon analysis of the feed results. Preferably, the virginiamycin is coated by microencapsulation. Any method of microencapsulation well known to the pharmaceutical art may be employed. For example, fluid bed coating or spray congealing may be employed to microencapulate the compound. Advantageously, the NCR process which is a chemical process based on coacervation techniques is the coating procedure employed.

The coating material employed in the microencapsulation of the antibiotics of this invention may be fatty acid, alcohol or ester, alone or an admixture thereof. More specifically, the fatty acid may have from 10 to 22 carbon atoms and may be, for example, decenoic, stearic, palmitic, lauric or myristic acid.

The fatty alcohols may have from 14 to 31 carbon atoms and may be, for example, lauryl alcohol, cetyl, stearyl, myristyl, carnubyl or ceryl alcohol.

The esters may be mono-, di-, or trigylceryl esters. The coating material may be modified by waxy materials of natural or synthetic sources. Exemplary of such waxes are beeswax, spermacetic wax or carnauba wax.

Additional coating materials that may be employed are for example, cellulose derivatives such as celluose acetate phthalate, ethyl cellulose, cellulose acetate butyrate, and Eudragit compounds such as copolymers of dimethylaminoethylmethacylate and neutral methacylic ester.

Preferably, the coating materials used in the microencapsulation process are gelatin, carboxymethylcellulose, cellulose acetate phthalate, starch, polyvinyl alcohol, and waxes.

The present invention is particularly well adapted for recovering antibiotics, such as, for example, virginiamycin, tetracyclines, streptomycin, penicillins, erythromycin, oleandomycin, bacitracin, streptogramin, synergistin, pristinamycin, mikamycin and ardicin.

In a preferred embodiment of this invention the antibiotic is virginiamycin and the coating material a mixture of gelatin and carboxymethylcellulose.

The microencapsulated (coated) virginiamycin of this invention was tested and compared with granulated virginiamycin. The coating material present in the microencapsulated form was gelatin and carboxymethylcellulose. Virginiamycin was granulated according to U.S. Pat. No. 3,627,885. Both the microencapsulated and granulated forms of virginiamycin were added to separate portions of the same basic cattle feed containing a high moisture content and the feed analyzed for virginiamycin recovery.

The analysis used was the conventional microbiological paper disk diffusion method on agar-agar using corynebeac-terium xerosis NCTC 9755 for determining the recovery of the antibiotic. The following example sets forth the procedure and results.

EXAMPLE

| Basic Cattle Feed | |
|---|---|
| Ingredients | Percent W/W |
| Corn Silage | 30.00 |
| Cracked Corn | 60.00 |
| Liquid Molasses | 5.00 |
| Cattle Pelleted Supplement | 5.00 |

All the ingredients were thoroughly blended for 15 minutes and the moisture checked. The moisture content was 25%.

To separate 10 pound samples of the above basic feed an equivalent amount of virginiamycin in a granulated (Stafac) and microencapsulated (coated) form was added. Each sample was stored in a sealed plastic bag and analyzed for percent virginiamycin recovery during a 14 day storage period at ambient temperature. The following results were obtained.

|  | Stafac (granulated) | Microencapulate (coated) |
|---|---|---|
| Initial Assay | 111.7% | 100.0% |
| Day 7 | 80.0% | 108.2% |
| Day 14 | 60.0% | 117.6% |

The results of this study clearly indicate that the microencapsulated or coated virginiamycin demonstrate significantly improved recoveries from a high moisture basic cattle feed than the granulated virginiamycin.

A further study was conducted to compare granulated and microencapsulated virginiamycin in a pelleted poultry feed diet containing high fat (10%) and fish meal.

| Basic Poultry Feed Formula | |
|---|---|
| Ingredients | % W/W |
| Ground Yellow Corn | 52.00 |
| Soybean Meal (44%) | 24.00 |
| Fish Meal | 3.00 |
| Dehydrated Alfalfa Meal (17%) | 5.00 |
| Distillers Dried Grains with Solubles | 2.00 |
| Dicalcium phosphate | 1.50 |
| Ground limestone | 1.50 |
| Plain Salt | 0.50 |
| DL-Methionine | 0.05 |
| Vitamin/Mineral Premix | 0.45 |
| Animal Fat | 10.00 |

The ingredients were thoroughly mixed and pelleted. To separate 10 pound samples of the above basic feed an equivalent amount of virginiamycin in a granulated (Stafac) and microencapulated (coated) form was added. Each sample was stored in 3 ply Kraft paper bags and analyzed for percent virginiamycin recovery during a 60 day storage period at ambient temperatures. The following results were obtained.

|  | Stafac (granulated) | Microencapulate (coated) |
|---|---|---|
| Initial Assay | 93.5% | 103.4% |
| Day 7 | 94.6% | 103.5% |
| Day 14 | 69.3% | 89.9% |

The results of this study clearly demonstrates the much improved recovery of microencapsulated virginiamycin over the granulated form (Stafac) from pelleted poultry feed containing high fat and fish meal.

What is claimed is:

1. A method for improving the recovery of antibiotics from animal feed composition said composition having a moisture content of from about 15 to about 30% and a fat content above 5% which comprises coating the antibiotic with a coating selected from the group consisting of gelatin; waxes; polyvinyl alcohol; a cellulose derivative represented by carboxmethylcellulose, cellulose acetate phthalate, ethyl cellulose and cellulose acetate butyrate; a fatty alcohol having from 14 to 31 carbon atoms; a fatty acid having from 10 to 22 carbon atoms; mono, di and tri glyceryl esters; and copolymers of dimethylaminoethylmethacrylate and neutral methacrylic esters and adding said coated antibiotic to a basic animal feed.

2. The method of claim 1 wherein said antibiotic is virginiamycin.

3. The method of claim 1 wherein said antibiotic is coated with a combination of gelatin and carboxymethylcellulose.

4. The method of claim 1 wherein said antibiotic is coated by microencapsulation.

* * * * *